United States Patent [19]

Finsterwald

[11] Patent Number: 4,861,242

[45] Date of Patent: Aug. 29, 1989

[54] SELF-LOADING PERISTALTIC PUMP

[75] Inventor: P. Michael Finsterwald, Denver, Colo.

[73] Assignee: Cobe Laboratories, Inc., Lakewood, Colo.

[21] Appl. No.: 87,096

[22] Filed: Aug. 19, 1987

[51] Int. Cl.[4] ............................................. F04B 43/12
[52] U.S. Cl. ..................................... 417/477; 417/476
[58] Field of Search ................ 417/477, 476, 475, 474

[56] References Cited

U.S. PATENT DOCUMENTS

| 4,178,138 | 12/1979 | Iles | 417/477 X |
|---|---|---|---|
| 4,221,543 | 9/1980 | Cosentino et al. | 417/477 X |
| 4,278,085 | 7/1981 | Shim | 417/477 X |
| 4,379,452 | 4/1983 | DeVries | 604/6 |
| 4,392,794 | 7/1983 | Foxcroft | 417/477 X |
| 4,472,116 | 9/1984 | Wenstrup | 417/477 |
| 4,545,744 | 10/1985 | Weber et al. | 417/477 X |
| 4,548,553 | 10/1985 | Ferster | 417/477 |
| 4,586,882 | 5/1986 | Tseng | 417/477 |
| 4,606,710 | 8/1986 | Maguire | 417/477 |
| 4,666,598 | 5/1987 | Heath et al. | 210/239 |

FOREIGN PATENT DOCUMENTS 0134436 6/1984 European Pat. Off. .

Primary Examiner—Carlton R. Croyle
Assistant Examiner—Eugene L. Szczecina

[57] ABSTRACT

A self-loading peristaltic pump including a rotor rotatably mounted about a rotor axis, and a race having an internal surface for supporting a flexible tube in a pumping region between the rotor and the race, the surface including points that are at equal radii from the rotor axis in planes that are perpendicular to the rotor axis, the rotor including a roller for intermittently and progressively compressing the flexible tube against the race in the pumping region, the rotor including a radially extending rotor tab located outside of the pumping region for displacing the flexible tube toward the pumping region as the rotor rotates.

14 Claims, 2 Drawing Sheets

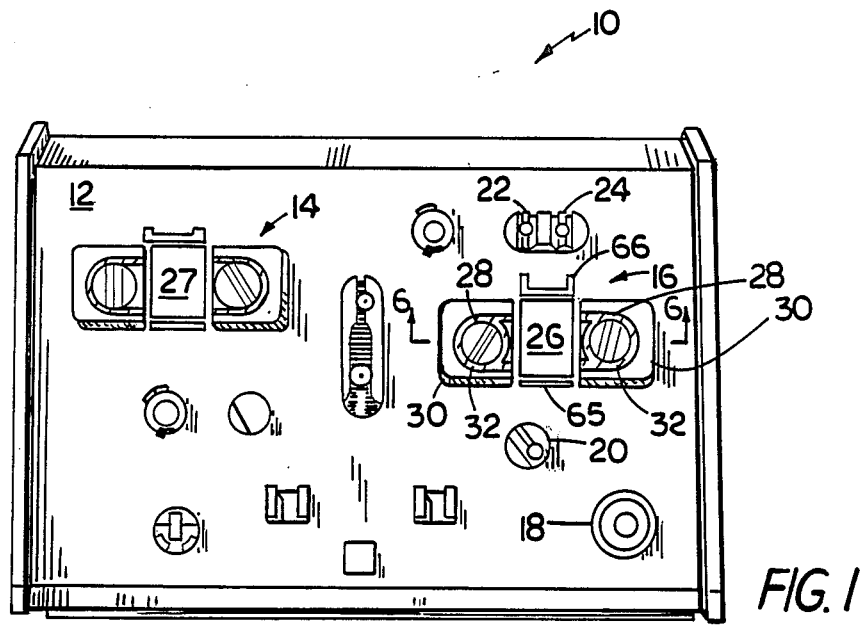
FIG. 1
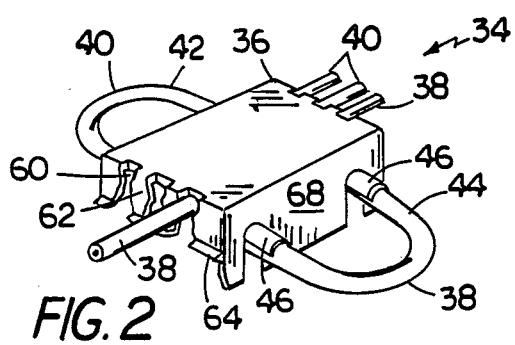
FIG. 2
FIG. 3
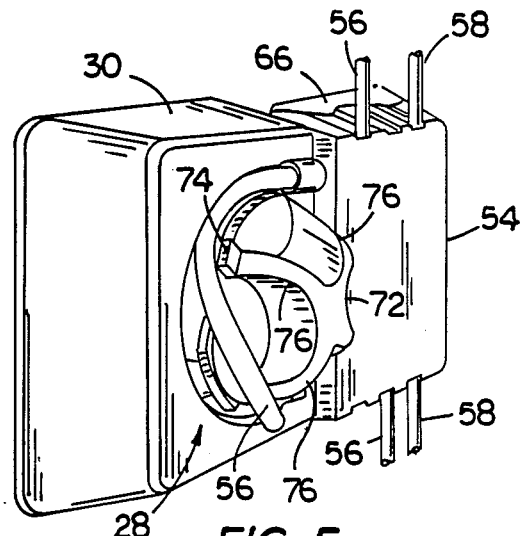
FIG. 5
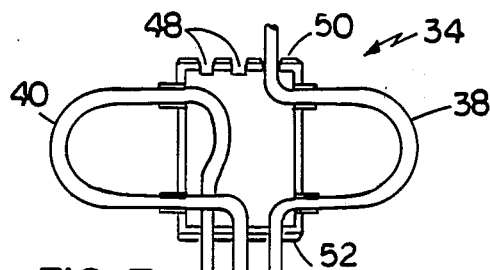
FIG. 4
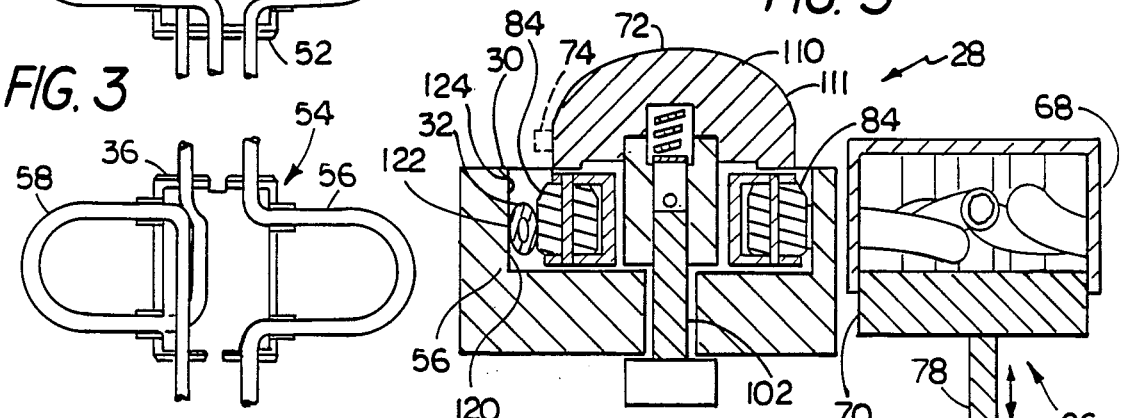
FIG. 6

SELF-LOADING PERISTALTIC PUMP

FIELD OF THE INVENTION

The invention relates to peristaltic pumps.

BACKGROUND OF THE INVENTION

In one type of peristaltic pump, a flexible tube is compressed between rollers that are carried by a rotor and travel along a circular path and a race that has a surface adjacent to and concentric with the path of the rollers. As the occluded portion of the tube is advanced, the fluid in front of it is forced to travel through the tube.

A use of such a pump is in extracorporeal blood treatment. The peristaltic pumps have been provided on the front panel of a blood processing machines, employing flexible tube portions of a disposable tubing set that is changed for use with a different donor/patient. Some tubing sets have included cartridges that are removably mounted on the machine and carry flexible tubes in position to be acted upon by pump rollers on the front panel of the machine, e.g., DeVries U.S. Pat. No. 4,379,452; published European Patent Application 0,134,436; Heath et al., U.S. Ser. No. 748,545, filed June 25, 1985; and Finsterwald et al., U.S. Ser. No. 860,539, filed May 7, 1986.

In the Finsterwald et al. '539 patent application, there is description of a pump that self-loads a flexible tube portion placed in a tube mounting region adjacent to a tube pumping region between the race and the rollers, as the rollers rotate, owing to the action of a small diameter roller portion adjacent to the tube mounting region and a large diameter roller portion adjacent to the tube pumping region. When unloading the tube from the pump, a lifter arm extending from a movable cover lifts the tube out of the tube pumping region as the cover is moved away from the pump.

SUMMARY OF THE INVENTION

It has been discovered that a removable, flexible tube can be self-loaded into the pumping region of a peristaltic pump between a rotor roller and a race by providing a radially extending rotor tab outside of the pumping region to displace the flexible tube toward the pumping region as the rotor rotates.

In preferred embodiments the roller includes a large diameter portion and a smaller diameter portion to cause the flexible tube to be self-aligning at the large diameter portion; a linear actuator is used to move the flexible tube in a direction parallel to the rotor axis so that the rotor tab engages the tube as the linear actuator moves the tube toward the pumping region and also engages the tube as the linear actuator moves the tube away from the pumping region to assist in lifting the tube out of the pumping region; the flexible tube is supported within and extends from a cartridge that is carried on a carriage that releasably engages the cartridge and is driven by the linear actuator; there are two rotors and races on opposite sides of the carriage and two flexible tubes extending from the cartridge to provide two pumps in a single apparatus; and the rotor includes a substantially dome-shaped rotor cap for guiding the flexible tube into engagement with the rotor tab as the linear actuator moves the tube toward the pumping region.

Other advantages and features of the invention will be apparent from the following description of a preferred embodiment thereof and from the claims.

DESCRIPTION OF THE PREFERRED EMBODIMENT

The preferred embodiment will now be described.

DRAWINGS

FIG. 1 is a perspective view of a front panel of a blood separation machine including a rotor and race for receiving a flexible tube portion carried by a cartridge in order to provide a peristaltic pump according to the invention.

FIG. 2 is a perspective view of a cartridge for mounting on the FIG. 1 machine and carrying tube portions for use in a peristaltic pump according to the invention.

FIG. 3 is a bottom view of the FIG. 2 cartridge.

FIG. 4 is a bottom view of an alternative cartridge having tubes threaded in a different way than the FIG. 2 cartridge.

FIG. 5 is a perspective view showing a portion of the FIG. 4 cartridge being loaded into a tube pumping region between a race and rotor of the FIG. 1 machine.

FIG. 6 is a partial vertical sectional view taken at 6—6 of FIG. 1 when a cartridge is mounted on the apparatus.

STRUCTURE

Figure 7:
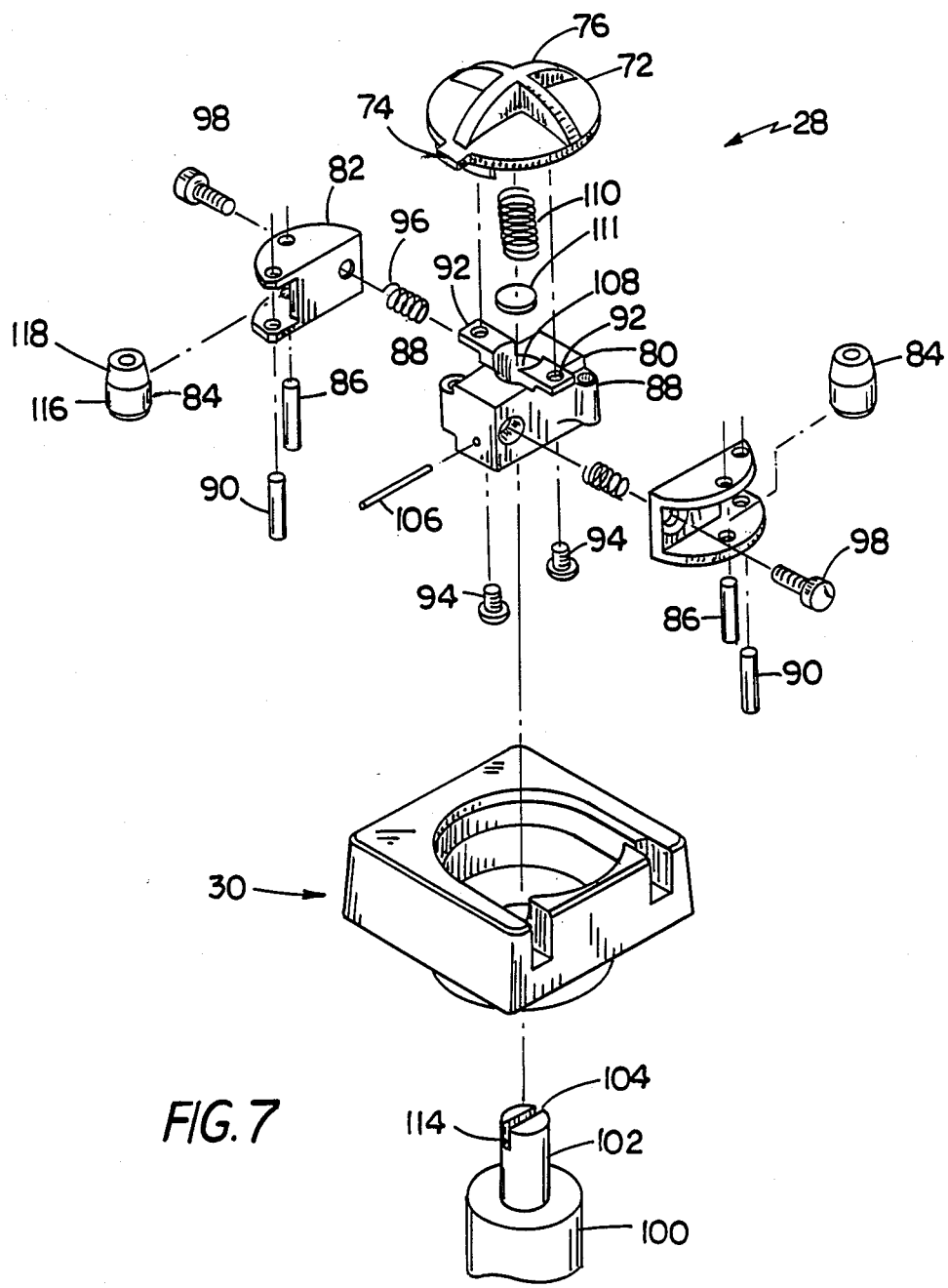
FIG. 7 is an exploded perspective view of a race and rotor of the FIG. 1 machine.

Referring to FIG. 1, there is shown centrifugal blood separation machine 10, including on its front face 12 two peristaltic pump units 14, 16 and various other components for interacting with components of a disposable tubing set (not shown) mounted on it, for example, platelet sensor 18, red blood cell return pinch valve 20, and 3-way plasma and collect pinch valves 22, 24. Pump units 14, 16 each includes a respective carriage 26, 27 for releasably engaging a respective cartridge 34, 54 (FIGS. 2, 4). Associated with, and on opposite sides of, each cartridge 34, 54 are two rotors 28 and corresponding races 30 defining tube pumping regions 32 therebetween for receiving U-shaped tube loops of the cartridges.

Referring to FIG. 2, there is shown cartridge 34, which is used with pump unit 14. Cartridge 34 includes plastic housing 36 and portions of two flexible tubes, anticoagulant tube 38 and blood inflow tube 40. These tubes are threaded through and supported within shell 36 and include U-shaped loops 42, 44 extending from opposite sides. Housing 36 includes four laterally extending curved guide supports 46 to which tubes 38, 44 are solvent bonded. Supports 46 maintain the tube portions between them in U-shaped loops. Housing 36 includes six slots 48, three at top wall 50 and three at bottom wall 52. In cartridge 34, one end of tube 38 extends upward from top wall 50 and is connected to a bag of anticoagulant (not shown) and the other end extends downward for joining with blood inflow tube 40 upstream of pump unit 14. Both ends of tube 40 extend from bottom wall 52 of housing 36. Pump cartridge 54, used with pump unit 16, employs an identical housing 36, but has a different tube arrangement; platelet tube 58 and plasma tube 56 each enter housing 36 through slots in the bottom wall and pass through respective slots in the top wall of housing 36. Both tubes 56, 58 have the same direction of flow (top to bottom)

for a given direction of rotation of rotors, even though the loops extend in opposite direction, because loop 58 overlaps itself. Slots 48 include aperture 60, large enough to hold a connecting portion of a tube therein without deformation of the tube, and narrow neck 62, which leads to aperture 60 and requires deformation of the tube when the tube passes through it. Top wall 50 and bottom wall 52 of housing 36 include tabs 64, for engaging recesses on carriage 26 in lower portion 65 and recesses in movable top portion 66. Side walls 68 of housing 36 extend downward further than top and bottom walls 50, 52 and are sized to mate with the outside surfaces of base plate 70 of carriage 26 (FIG. 6).

Referring to FIGS. 5, 6, and 7, it is seen that rotor 28 includes cap 72 having radially extending tab 74 outside of tube pumping region 32. In FIG. 6, tab 74 is shown in phantom and rotated 90° from its true position with respect to rollers 84 (as can be seen from FIG. 7). Cap 72 also has four outwardly curved ribs 76, making cap 72 substantially dome-shaped. Carriage base 70 is connected for vertical movement to linear actuator shaft 78. Linear actuator shaft 78 is connected to motor 79, which drives shaft 78 and thus carriage 26. Referring to FIG. 7, rotor 28 includes base 80 and a pair of pivotally mounted yokes 82 for rotatably supporting rollers 84 about shafts 86. Yokes 82 are pivotally mounted at ears 88 of base 80 via pins 90. Cap 72 is secured to ears 92 of base 80 via screws 94. Yokes 82 are spring biased radially outward via compression springs 96 and are prevented from unlimited outward travel via stop screws 98. Variable speed motor 100 includes motor adapter shaft 102, which passes vertically through vertical hole 108 of base 80 and has a bayonet-type slot 104 for releasably engaging pin 106, which is secured to base 80 and passes through hole 108. Compression spring 110 is between cap 72 and plate 111, which rests on the top of adapter shaft 102. Spring 110 biases base 80 upward, thereby locking pin 106 in vertically directed end 114 of bayonet slot 104. Each roller 84 has 0.50" high and 0.480" diameter cylindrical large diameter portion 116 and 0.360" to 0.365" high conical smaller diameter portion 118 having a 4°±30' angle and ending at a diameter of 0.429" at its top. Tab 74 extends outward from cap 72 (which is 1.80" in diameter) by 0.100". Inner surface 120 of race 30 includes a large diameter portion 122 and a conical small diameter portion 124 having a similar shape to roller 84.

Operation

In operation, a disposable tubing set including cartridge 34 and cartridge 54 is mounted on machine 12, the mounting including snapping cartridge 34 onto carriage 27 of pump unit 14 and snapping cartridge 54 onto carriage 26 of pump unit 16, the tabs 64 engaging respective recesses at bottom 65 and top 66 of carriages 26, 27. U-shaped tube loops 42, 44 are initially outward of tab 74 (i.e., above tab 74 in FIG. 6), linear actuator shaft 78 being raised upward in an initial preloading position. U-shaped tube loops 42, 44 are loaded into pump units 14, 16 by rotation of rotors 28 and movement toward the face of machine 12 of linear actuater shaft 78. As tube loops 42, 44, are moved toward the face of machine 12, the curved portions of the loops are guided by dome-shaped ribs 76 and eventually move into the path of travel of tabs 74 and are engaged by them and displaced toward tube pumping region 32 between the rollers and the race as shown in FIG. 5. The tube is brought into contact with conical small diameter portion 118 of roller 84, and then travels along the surface of conical portion 118 toward the larger diameter base of conical portion 118 and self-aligns at large diameter portion 116, owing to the difference in radius of the portions of the rollers, as linear actuator continues downward to the position shown in FIG. 6. Tube loops 42, 44 maintain their aligned positions at large diameter portions 116 of rollers 84. Because a continuous tube is used, there are no junctions or connections to different pieces of tubing, simplifying manufacture and providing a smooth flow path without sharp edges for the blood and separated blood components, reducing chance of damage to blood components.

To unload tube loops 42, 44, rotor 28 rotates while linear actuator 78 moves the cartridge outward from the front panel of the machine. The straight leg portions of U-shaped tube loops 42, 44 thus also tend to be pulled outward, while the portions engaged by the roller tend to be maintained at the large diameter portion. Eventually each tab 74 engages a respective lower surface of tube loop 42 or 44 near the junction of the straight leg portion with the portion engaged by the rollers and lifts it up outward, preventing engagement by the following roller.

OTHER EMBODIMENTS

Other embodiments of the invention are within the scope of the following claims.

What is claimed is:

1. A self-loading perstaltic pump comprising:
   a rotor rotatably mounted about a rotor axis, and
   a race having an internal surface for supporting a flexible tube in a pumping region between said rotor and said race, said surface including points that are at equal radii from said rotor axis in planes that are perpendicular to said rotor axis,
   said rotor including at least one roller for intermittently and progressively compressing said flexible tube against said race in said pumping region, each said roller comprising a large diameter roller portion adjacent to a smaller diameter roller portion, the shape of each said roller causing said flexible tube to be self-aligning at said large diameter portion,
   said rotor including a radially extending rotor tab located outside of said pumping region for displacing said flexible tube toward said pumping region so as to be engaged by said smaller diameter portion as said rotor rotates,
   said smaller diameter portion being located closer to said radially extending tab than said large diameter portion.

2. The pump of claim 1 wherein said roller is rotatably mounted about a roller axis, said roller axis being parallel to said rotor axis.

3. The pump of claim 2 wherein there are a plurality of rollers, each said roller being rotatably mounted about a roller axis, each said roller axis being parallel to said rotor axis.

4. The pump of claim 1 wherein said internal race surface includes a large diameter race portion aligned with said large diameter roller portion and a smaller diameter race portion aligned with each said smaller diameter roller portion.

5. The pump of claim 1 wherein said large diameter roller portion is cylindrical and each said smaller diameter roller portion is conical.

6. The pump of claim 1 wherein said rotor is releasably mounted.

7. The pump of claim 6 further comprising a rotational actuator for rotating said rotor, said rotational actuator having a slotted shaft, said rotor lockably engaging said slotted shaft.

8. The pump of claim 7 wherein said rotational actuator is a variable speed motor.

9. A self-loading pump comprising
a rotor rotatably mounted about a rotor axis,
a race having an internal surface for supporting a flexible tube in a pumping region between said motor and said race, said surface including points that are at equal radii from said rotor axis in planes that are perpendicular to said rotor axis,
said rotor including at least one roller for intermittently and progressively compressing said flexible tube against said race in said pumping region,
said rotor including a radially extending rotor tab located outside of said pumping region for displacing said flexible tube toward said pumping region as said rotor rotates, and
a linear actuator for moving said flexible tube in a direction parallel to said rotor axis, whereby said rotor tab engages said tube as said linear actuator moves said tube toward said pumping region to load said tube, and said rotor tab also engages said tube as said linear actuator moves said tube away from said pumping region to assist in moving said tube away from said pumping region to unload said tube,
said flexible tube being supported within and extending from a cartridge,
said linear actuator including a motor that drives a carriage for releasably engaging said cartridge.

10. The pump of claim 9 wherein there are two said rotors and races on opposite sides of said carriage, and there are two flexible tubes extending from said cartridge, said tubes having U-shaped portions sized for fitting in respective tube pumping regions.

11. The pump of claim 8 wherein said rotor comprises a substantially dome-shaped rotor cap for guiding said flexible tube into engagement with said rotor tab as said linear actuator moves said tube toward said pumping region.

12. A method of loading a flexible tube into a peristaltic pump, said pump having a rotating rotor and a race having an internal surface for supporting the tube in a pumping region between the rotor and the race, comprising:
forming the flexible tube into a U-shaped loop parallel to the plane of rotation of said rotor by providing the tube on a cartridge,
moving said tube loop toward said pumping region by a linear actuator including a motor that drives a carriage that releasably engages said cartridge,
providing a projecting tab on said rotor,
engaging said tube loop with said tab, and
displacing said tube loop toward said pumping region by said tab as said loop is moved toward said pumping region by said linear actuator.

13. The method of claim 12 further comprising:
providing a roller in said rotor having a large diameter roller portion adjacent to a smaller diameter roller portion, and
self-aligning said tube loop at said large diameter portion.

14. A method of unloading a U-shaped flexible tube from a peristaltic pump, the pump having a rotating rotor and a race having an internal surface for supporting the tube in a pumping region between the rotor and the race comprising:
moving said tube loop away from said pumping region by a linear actuator including a motor that drives a carriage that releasably engages a cartridge on which said tube is carried,
providing a projecting tab on said rotor,
engaging said tube loop with said tab, and
lifting said tube loop out of said pumping region with said tab as said loop is moved away from said pumping region by said linear actuator.

* * * * *